United States Patent [19]

Klehm

[11] Plant 4,233

[45] Apr. 4, 1978

[54] PEONY PLANT NAMED MY PAL RUDY

[75] Inventor: Roy G. Klehm, Barrington, Ill.

[73] Assignee: Klehm Boys' Partnership, Arlington Heights, Ill.

[21] Appl. No.: 787,714

[22] Filed: Apr. 14, 1977

[51] Int. Cl.[2] ..... A01H 5/00

[52] U.S. Cl. ..... Plt./68

[58] Field of Search ..... Plt./68

*Primary Examiner*—Robert E. Bagwill

[57] ABSTRACT

A new variety of peony plant having medium sized midseason blooms combining a near perfect rose-type peony flower form with beautiful soft Venetian pink colors and above average lasting qualities both on the plant and as cut flowers. The blooms are carried on strong, weather-resistant stems and the foliage of the plant is clean and attractive which enhances the total reliability and dependability of this variety over a wide geographical area.

1 Drawing Figure

BACKGROUND OF THE NEW PLANT

This new peony plant was discovered by applicant at his breeding grounds in Arlington Heights, Ill., this plant being a seedling of Mons. Jules Elie × W. L. Gumm (both unpatented) resulting from a cross made by applicant in the course of breeding efforts carried on by him at Arlington Heights, Ill., with the objective of producing improved, fully double, rose-type peony flowers on plants having stiffer, stronger and more weather-resistant stems and a reliable yearly performance in a wide geographic area.

Observation of many generations of asexually propagated plants of this new plant, produced by applicant and under his direction at Arlington Heights, Ill., has shown that its distinctive and advantageous characteristics are carried intact from generation to generation and appear to be firmly fixed. Because of its apparent market value as a garden flower, production of this new variety on a commercial scale is now being carried on, by means of root division, at Arlington Heights, Ill., and at production grounds at Champaign, Ill.

DESCRIPTION OF THE DRAWING

This new variety of peony plant is illustrated by the accompanying photographic drawing which, in full color, shows a full view of the blossom of the new plant, the colors shown being as nearly true to that of the living flower as it is reasonably possible to obtain through conventional professional photographic procedures.

DESCRIPTION OF THE PLANT

The following is a detailed description of applicant's new variety of peony plant with color specifications according to the R.H.S. Colour Chart published at London, England, by The Royal Horticultural Society with the collaboration of the British Colour Council, the observations hereinafter set forth having been made at Arlington Heights, Ill., in the late Spring of 1976.

THE PLANT

Origin: Seedling.
Parentage:
*Seed parent.*—Mons. Jules Elie (unpatented).
*Pollen parent.*—W. L. Gumm (unpatented).
Classification: *Paeonia Lactiflora.*

Form: Bush, of generally round shape.
Height: 38 to 42 inches.
Growth: Vigorous, sturdy and upright.
*Strength.*—Very good.
*Cane size.*—Averaging about ½ inch.
Foliage: Abundant with numerous leaves.
*Leaf size.*—Medium.
*Shape.*—Elliptically acute.
*Aspect.*—Glossy and smooth.
*Color.*—Clean Almond Green — R.H.S. 36B.

THE BUD

Size: Large.
*Diameter.*—1⅛ to 1¼ inch.
*Depth.*—About 1⅛ inch.
Form: Globular and round.
Opening rate: Generally average depending on weather — somewhat slower in warmer climate.
Color:
*When sepals first divide.*—Dawn Pink — R.H.S. 49B.
*When sepals begin to unfurl.*—Venetian Pink — R.H.S. 49C.
Sepals: Hooded over bud until dividing.
*Color.*—Inside — Scheeles Green — R.H.S. 144B. Outside — Green — R.H.S. 144C.
Calyx:
*Shape.*—Polysepalous.
*Size.*—Very large.
*Aspect.*—Smooth.
*Splitting.*—The calyx does not split.

THE FLOWER

Blooming habit: The flowers bloom once each year in mid-Spring.
Borne: In a cluster comprising one central flower with generally three axillary buds on each stem.
Size: Medium.
*Diameter.*—6½ to 7¼ inches.
Shape: Cup-shaped when bloom first opens, becoming a fully double rose-type flower as the bloom matures.
Petalage: Multitudinous.
*Arrangement.*—Imbricated.
*Form.*—Spatulate. Margin Type: Generally smooth, about 10% with notched guard petals.
*Texture.*—Soft.
*Aspect.*—Shiny satiny.

*Color* (*all petals*).—Upper Side — Orient Pink — R.H.S. 36A-36B. Reverse Side — Venetian Pink — R.H.S. 49C.

Fragrance: Mild peony type.

Persistence: Complete dehiscence — when flower reaches its term the petals drop off completely.

Disease resistance: This plant has high resistance to leaf blotch and fungus bud diseases as observed at Arlington Heights, Ill., and Champaign, Ill., where such diseases are found to be present.

Lasting quality: Above average on plant and as cut flowers.

REPRODUCTIVE ORGANS

The flowers of this plant have no reproductive organs.

The unique and distinct characteristic of this new variety of peony plant resides in its combination of a beautiful soft Orient pink blossom coloration with a nearly perfect rose-type flower of relatively large size borne on strong, weather-resistant stems. Also, the dependability of this new variety is materially enhanced by its clean and attractive foliage.

I claim:

1. The new and distinct variety of peony plant substantially as herein shown and described, characterized by the rose-type flower form of its blooms combined with their soft pink coloration, the strong weather-resistant stems on which the blooms are borne, the above average lasting quality of the blooms, and the clean and attractive plant foliage.

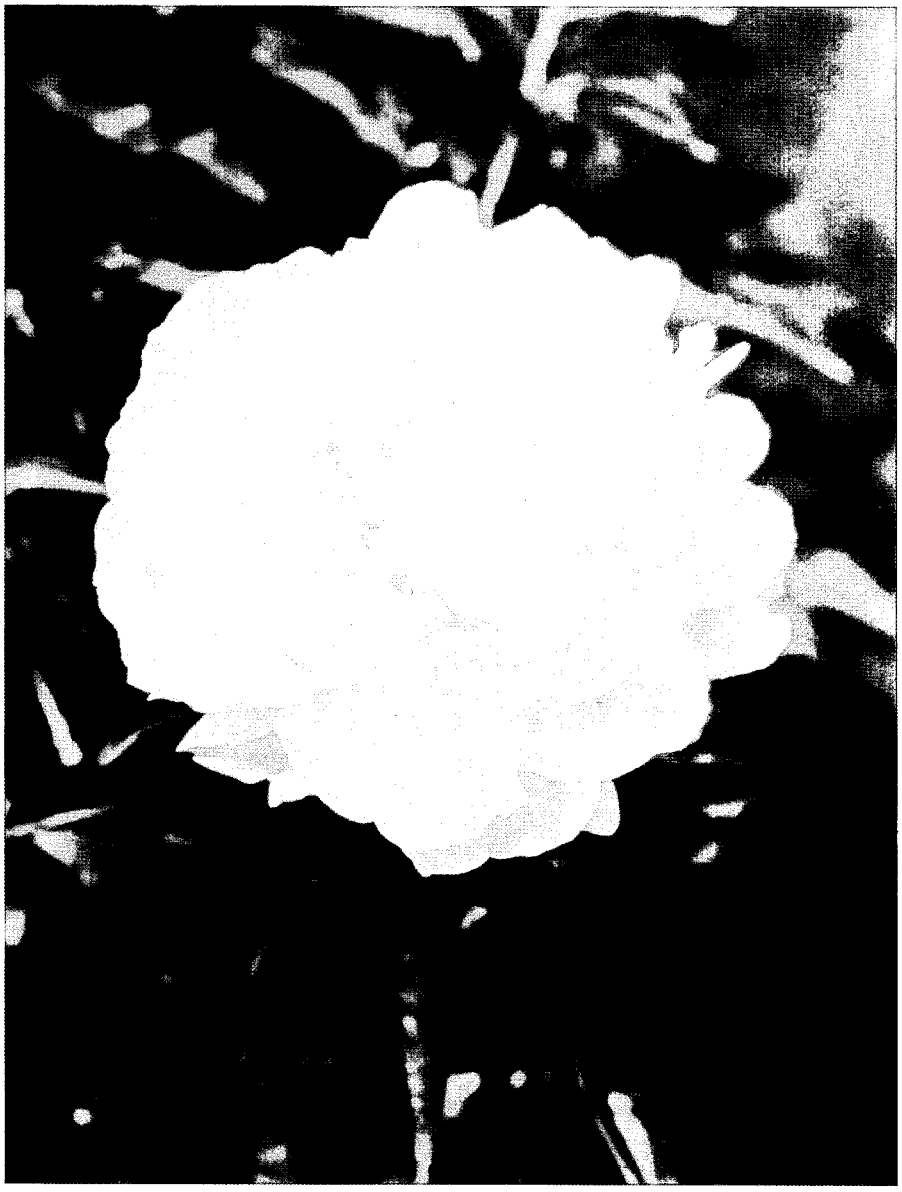

* * * * *